(12) United States Patent  (10) Patent No.: US 7,997,139 B2
Owens et al.  (45) Date of Patent: Aug. 16, 2011

(54) GUIDED WAVE PIPELINE INSPECTION SYSTEM AND METHOD WITH ENHANCED NATURAL FOCUSING TECHNIQUES

(75) Inventors: Steven E. Owens, Bellefonte, PA (US); Li Zhang, Bellefonte, PA (US); Joseph L. Rose, State College, PA (US)

(73) Assignee: FBS, Inc., State College, PA (US)

( * ) Notice: Subject to any disclaimer, the term of this patent is extended or adjusted under 35 U.S.C. 154(b) by 505 days.

(21) Appl. No.: 12/327,717

(22) Filed: Dec. 3, 2008

(65) Prior Publication Data

US 2009/0139337 A1    Jun. 4, 2009

Related U.S. Application Data

(60) Provisional application No. 60/991,947, filed on Dec. 3, 2007.

(51) Int. Cl.
*G01N 29/04* (2006.01)
*G06F 19/00* (2011.01)

(52) U.S. Cl. ............... 73/622; 73/579; 73/599; 73/602; 702/39; 702/56

(58) Field of Classification Search .................. 73/622, 73/579, 597, 599, 600, 602; 702/39, 56
See application file for complete search history.

(56) References Cited

U.S. PATENT DOCUMENTS

| | | | |
|---|---|---|---|
| 4,055,990 A | 11/1977 | Topping | |
| 4,127,035 A | 11/1978 | Vasile | |
| 4,439,730 A | 3/1984 | Kaufman | |
| 4,769,598 A | 9/1988 | Krieg et al. | |
| 4,945,306 A | 7/1990 | Lowther | |
| 5,359,898 A * | 11/1994 | Latimer | 73/600 |
| 6,079,273 A * | 6/2000 | Latimer et al. | 73/622 |
| 6,138,514 A * | 10/2000 | Iwamoto et al. | 73/622 |
| 6,404,189 B2 | 6/2002 | Kun et al. | |
| 6,568,271 B2 * | 5/2003 | Shah et al. | 73/599 |
| 7,299,697 B2 * | 11/2007 | Siddu et al. | 73/597 |
| RE40,515 E * | 9/2008 | Kwun et al. | 324/220 |
| 7,474,092 B1 * | 1/2009 | Kwun et al. | 324/238 |
| 7,950,298 B2 * | 5/2011 | Lavoie et al. | 73/866.5 |
| 2009/0150094 A1 * | 6/2009 | Van Velsor et al. | 702/39 |

FOREIGN PATENT DOCUMENTS

| | | |
|---|---|---|
| EP | 0304053 B1 | 2/1989 |
| EP | 0389877 A | 10/1990 |
| JP | 2009236794 | * 10/2009 |

* cited by examiner

*Primary Examiner* — J M Saint Surin

(74) *Attorney, Agent, or Firm* — Duane Morris LLP

(57) ABSTRACT

A method for the nondestructive inspecting of coated or uncoated pipeline, using ultrasonic guided waves excited on the outer or inner pipe surface, wherein at least one or more transducers are individually or simultaneously excited to generate ultrasound, wherein multiple received signals with different focal spot positions are processed and combined to produce a reduced number of final waveforms that show defect axial positions in the pipe, wherein a data calibration scheme is utilized to adjust velocity variability for all the guided wave modes at different frequencies, and wherein the hardware arrangement has at least one pulser channel and one receiver channel for the collection and storage of signals.

23 Claims, 15 Drawing Sheets

GUIDED WAVE PIPELINE INSPECTION SYSTEM AND METHOD WITH ENHANCED NATURAL FOCUSING TECHNIQUES

CROSS REFERENCE TO RELATED APPLICATIONS

The present application claims priority under 35 U.S.C. 119(e) to U.S. Provisional Patent Application 60/991,947 filed on Dec. 3, 2007, the entirety of which is incorporated by reference herein.

FIELD OF THE INVENTION

Aspects of the invention relate to pipeline inspection. More specifically, aspects of the invention relate to providing a quick, easy-to-use, guided wave pipeline inspection system and method to detect small defects, with varying frequencies, for example from 150 kHz to 800 kHz. The system utilizes enhanced frequency tuning, natural focusing techniques, and multi-mode detection capabilities.

BACKGROUND INFORMATION

Corrosion is one of the primary preventable causes of failure in refinery, petrochemical, and other pipelines. Cracking is also possible. Defects in pipelines have various shapes and locations. The defects, therefore, may be detectable for some guided waves at particular frequencies but non-detectable for other particular frequencies.

The Magnetic-Flux Leakage (MFL) method is currently the dominant technology for the in-line inspection (ILI) of transmission pipeline. Quite often, however, it is not possible to use ILI. As a consequence, Long Range Ultrasonic Guided Wave Inspection Systems have been developed. These systems have the capability of finding defects that range between 3% to 9% cross sectional area (CSA). These Long Range Ultrasonic Guided Wave Inspection Systems are currently difficult to use and somewhat time consuming as well. There is a need, therefore, to provide a cost efficient system and method that will identify defects in structures.

SUMMARY

It is therefore an objective of an aspect of the invention to provide a reliable method and apparatus for detecting small defects in piping from 0.1% to 3% CSA.

It is also an objective of an aspect of the invention to provide a more accurate and reliable method for crack and corrosion detection than is presently available through collections of hundreds of signals with signal processing to a single display.

In an example embodiment, an extremely easy-to-use pipe inspection system is provided.

In a further objective of the aspect of the invention, the method and system create and use many frequencies to more easily find the wave resonance of the defect that is the preferred frequency to produce a larger scattering echo response from the defect of type or size.

In a further example embodiment, the method and system perform a complete screening of the pipe being inspected for potentially serious defect sites.

In another example embodiment, the method and system are configured to inspect pipelines that are difficult to access or are partially hidden, by using a single sensor location, even if only partially around the pipe.

In a further example embodiment, the method and system are configured to provide or use ultrasonic sensors of any type, including piezoelectric longitudinal or shear transducer and electromagnetic acoustic transducers (EMATs), to carry out a pipe inspection.

An aspect of the invention creates an easy-to-use pipe inspection system capable of detecting defects much smaller than 3% CSA. A simplified data acquisition concept is presented for pipe inspection, whereby hundreds of signals can be collected, thereby exciting different groups being sensitive to different kinds of defects. No special processing is required to lead to a single display that is easy to interpret.

A natural focal point is moved all over the pipe circumferentially and axially and even over all sections of an elbow region, for example. Furthermore, the wave form will focus throughout the thickness of the pipe wall, as the wave form also changes as a function of frequency. Different natural focal point positions are possible by changing segment circumferential lengths, sensor positions, loading lengths, and frequency. Assembling all of the waveforms leads to a clear single display. If the group velocities of inspection waves change during frequency tunings, the reflection signals may be calibrated based on pre-calculated dispersion curves.

An ultrasonic guided wave generation system for pipeline inspections is presented. The system contains abundant transducers, that can be individually or simultaneously excited. The transducers are mounted on wedges with optimum incident angles, that are used to control the generated wave modes. Comb type sensor elements and/or Electro Magnetic Acoustic Transducers (EMATS) may also be used. By indexing, the data acquisition process is repeated after small increments around the circumference.

There are infinite numbers of possible guided wave modes in a pipeline. These wave modes in a pipe have different velocities and energy distributions, that may vary with frequency and/or excitation conditions. There are three mode types of time harmonic guided waves in hollow cylindrical media: 1. the axisymmetric longitudinal modes L(0,n), 2. axisymmetric torsional modes T(0,n), and 3. the flexural longitudinal $F_L(m,n)$ and torsional modes $F_T(m,n)$ (m=1, 2, 3, ... ; n=1, 2, 3, ... ). The longitudinal and torsional modes are axisymmetric. The flexural modes are non-axisymmetric and may appear in either longitudinal or torsional mode groups. The generated wave velocity is determined by the incident angle of the wedges or element spacing of the comb transducers or electromagnetic acoustic transducers (EMATs). These incident angle and spacing may be selected by using Snell's law of physics and mechanics.

If applying a partial loading, an infinite number of guided wave modes may be excited in a pipeline. The waves in a wave group usually have similar wave structures (known as energy distributions in the radial direction) and velocities at a particular frequency. According to guided wave theory, one single mode group may be selected within a particular frequency range by using an angle beam transducer with a proper wedge. Guided wave pipeline inspections with a single mode group may have clean reflection signals and fewer false alarms. It is important for the case of frequency tuning that a region is selected where the group and phase velocity curves are both flat over the desired frequency tuning range. If this does not occur, the mode will either not be excited at all of the excitation frequencies, or the velocity will change with frequency, and make interpretation difficult.

The energy distributions in the circumferential direction are called angular profiles. Because the flexural modes (also known as non-axisymmetric modes) have non-axisymmetric energy distributions, the angular profiles of a mode group may vary with changes of frequency, distance, and loading conditions. At some position, the energy is naturally concentrated at one or a few spots, so defects at these spots have a better chance to be detected. This phenomenon is called natural focusing. By tuning a frequency over a sufficient range and changing loading conditions, one can vary the natural focusing points and optimize the energy for defect detection. In addition, by moving the transducer location along the circumference of the pipe, the inspection energy at some spots may be improved and the entire pipe can be thoroughly scanned. This technique is called frequency and angle tuning (FAT).

The system presented herewith has several improvements beyond the FAT technique: The guided waves are transmitted by one sensor/transducer at a time, but they are received by all the sensors. Therefore, complete information is recorded and no defect echo is missed.

Furthermore, the system involves many different circumferential lengths and positions of transmitters, so inspection results are improved. Transmitters with variable circumferential loading lengths provide different energy distribution, especially angular profiles, at the same frequency and axial distance. Different loading positions also change energy distributions. By exciting a single transducer or N (N is a positive integer and no more than the maximum transducer numbers in the system) transducers together, the system gives many different angular profiles at each inspection spot and I achieves better inspection potential in pipelines.

Furthermore, guided wave inspections for elbowed pipelines are improved. The wave mode conversions at elbow regions may cause false alarms and decrease inspection energy. Based on theoretical simulations of the mode conversions, the system is designed to minimize the mode conversions and enhance the inspection results by achieving natural focusing at the regions in and beyond elbows.

Furthermore, based on theoretical analysis, the system involves thousands of inspection signals by applying frequency tuning over optimum ranges, variable excitation and receiving locations, and different loading lengths. After post processing and summing these signals, the user can obtain optimized, high-quality pipe inspection results, that have better defect sensitivity and fewer false alarms than the traditional axisymmetric inspection method. Signal averaging may be employed to improve signal-to-noise ratio by reducing random noise components.

The system and method also improves on the FAT technique by simplified display technology. The original FAT technique involved the user looking at thousands of waveforms. By selecting a region that is non-dispersive and therefore having a constant velocity over the frequency range, it is possible to combine all of the waveforms into a single result. One technique is to take an envelope of all of the waveforms collected and then take the maximum value received at each discrete point in time for the entire set of waveforms. This will result in one single waveform for the user to view, verses thousands. This is an example of one method of combining the waveforms, but the technique is not limited to this single method. The advantage of this technique is drastically reduced inspection time, and a reduced probability of user error.

It is important for the case of frequency tuning that a region is selected where the group and phase velocity curves are both flat or almost flat over the desired frequency tuning range. If this is untrue, the mode will either not be excited, or the velocity will change with frequency, and make interpretation difficult. If a dispersive region is selected, a velocity compensation algorithm will be needed for those frequencies, to obtain proper axial positioning of the reflector.

More than one wave group with various velocities may be used by the system to inspect pipe. The system is designed to only excite one mode group with all the modes having close group and phase velocities at each frequency. Based on the pre-calculated group velocity dispersion curves, the system determines the location of a reflector based on the velocity of the excited mode at a particular frequency.

The frequency tuning range may be selected to focus throughout the thickness of the pipe wall, by selecting a mode and frequency range where wave structure changes appropriately.

In one embodiment, a method for examining a pipe, is presented comprising arranging and pulsing sensors around a circumference of a pipe that when varying a number and position of sensors that are excited at least singularly, creates at least one of axisymmetric and non-axisymmetric wave forms and natural focal points in at least one of pipe, in pipe elbows, and beyond pipe elbows and when multiplexed around a circumference of the pipe, moves a focal spot to different positions in the pipe to find defects in the pipe wherein interpretation of results of received wave forms is made in a more timely manner by combining resulting waveforms into a single waveform or reduced number of waveforms.

In another embodiment, the method may further comprise frequency tuning to move the natural focal points to different positions throughout the pipe, wherein wave structures excited by the sensors are changed to enhance detection sensitivity for various defects in the pipe.

In another embodiment, the method may further comprise changing a receiving element region by varying numbers of sensors that are received and their positions around the circumference of the pipe to receive all possible modes that are reflected.

In another embodiment, the method may further comprise signal processing wherein multiple signals with different focal spot positions are processed and combined to produce a reduced number of final waveforms that show defect axial positions in the pipe.

In another embodiment, the method may be accomplished, wherein multiplexing a sending and receiving of the sensors around the circumference of the pipe produces and receives multiple non-axisymmetric waveforms with different focal spot positions that when received are processed and combined to lead to a reduced number of waveform displays.

In another embodiment, the method may be accomplished, wherein the sensors are pulsed to generate non-axisymmetric modes with natural focal spots with just partial loading of the pipe in a circumferential direction, thereby providing an ability to inspect at least one of hidden and inaccessible pipeline structures.

In another embodiment, the method may be accomplished, wherein the method detects defects that are approximately 0.1% cross sectional area and above over a frequency range 200 kHz to 800 kHz.

In another embodiment, the method detects defects that are approximately 3% cross sectional area and above over a frequency range 20 kHz to 150 kHz.

In another embodiment, the method detects defects that are approximately 0.01% cross sectional area and above in a thin walled tube using frequencies higher than 800 kHz.

In another embodiment, the method is used to determine defects in a pipe elbow.

In another embodiment, the method is accomplished wherein an excitation region is swept through phase velocity dispersion curve space in a horizontal direction for selected phase velocity values using angle beam wedges and frequency sweeping.

In another embodiment, the method may be conducted, wherein an excitation region is swept along an angled line of slope d from an origin through phase velocity dispersion curve space by using comb or EMAT sensors with a specific sensor element spacing that correlates to a slope d.

In another embodiment, the method is accomplished wherein there is partial loading only around a circumference of the pipe and given sufficient bandwidth, inspection of a complete circumference of the pipe is still provided along a length of the pipe. In another embodiment, shear type and longitudinal type sensors may be used.

In another embodiment, the method is accomplished wherein a phased array comb type transducer is placed on one of an angle beam wedge and directly onto a pipe surface in an abundant sensor arrangement around a circumference of the pipe to produce horizontal activation lines in dispersion curve space, each line determined by a unique set of time delays in each comb sensor and the wedge angle when a wedge is used. In another embodiment, the method is accomplished wherein additional time delays are applied to each comb sensor around the circumference of the pipe added to the set of time delays used to generate the specific horizontal activation line, to produce phased array focal spots in the pipeline in addition to new natural focusing spots.

In another embodiment, the method is accomplished such that it further comprises searching a phase velocity dispersion curve space and isolating positions where defects are found, wherein when a dispersive mode is used, defect location analysis is performed.

In another embodiment, the method is accomplished wherein the pipe is fluid loaded, wherein dominant inplane displacement on an inner surface is purposely excited to allow for inspection to occur, defect detection sensitivity is decreased such that only larger defects are found because of energy leakage to the fluid inside the pipe.

In another embodiment, EMAT shear sensors are used to reduce energy leakage to a fluid inside the pipe, therefore maintaining sensitivity to find defects.

In another embodiment, the method is conducted so that it further comprises utilizing partial loading around a circumference of the pipe that with one signal finds a defect at some particular axial and circumferential position around the pipe at a distance.

In another embodiment, the method is conducted so that it further comprises utilizing predicted focusing profiles for partial loading to determine a circumferential position of a defect.

In another embodiment, the method is conducted so that it further comprises changing a receiving element region by varying at least one of the number of sensors that are received and their position around the circumference of the pipe to receive all possible modes that are reflected.

DETAILED DESCRIPTION

Figure 1:
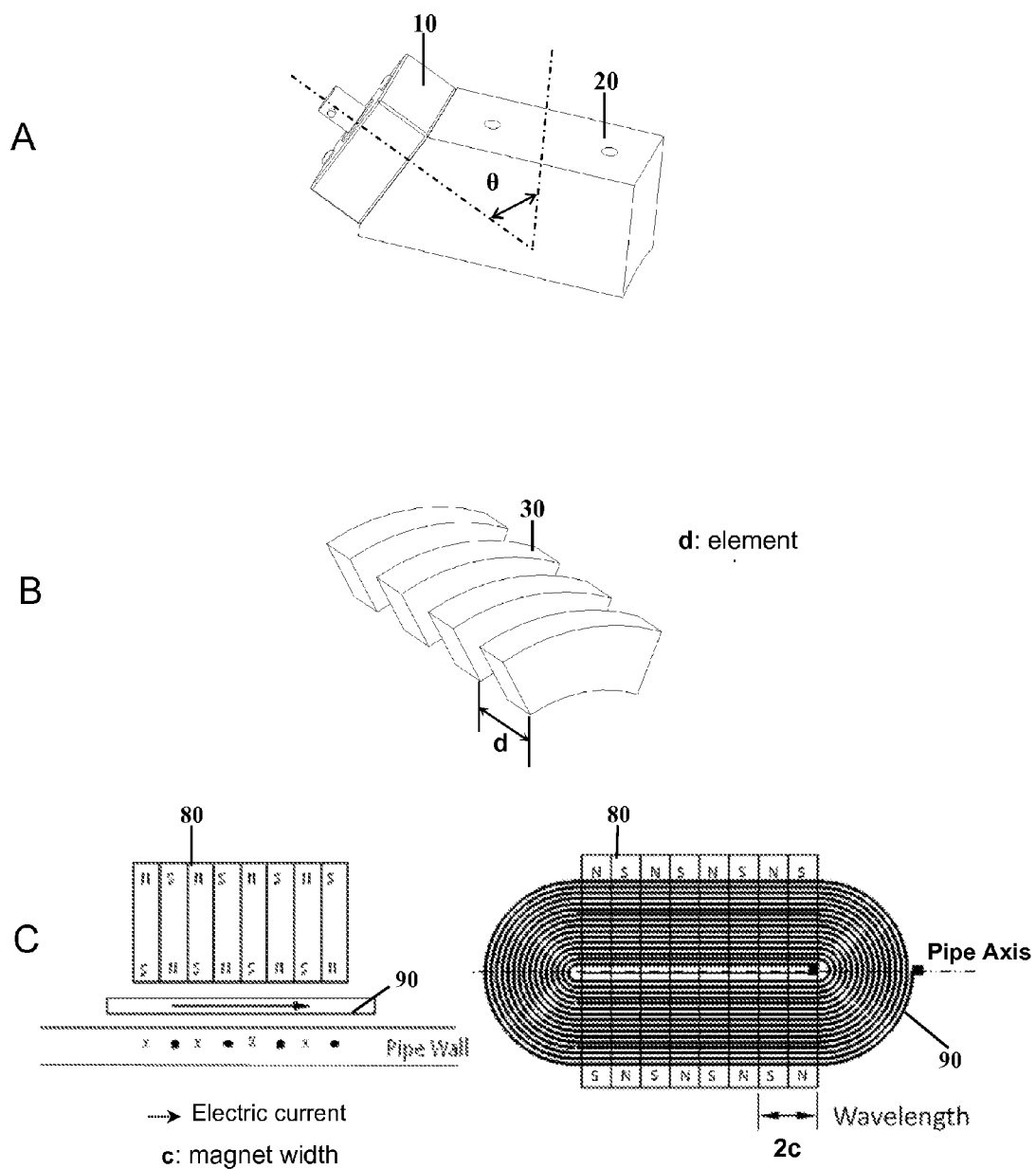
FIGS. 1A, 1B, and 1C are schematics of a typical angle beam transducer, comb transducer, and electromagnetic acoustic transducer (EMAT).

Referring to FIGS. 1A, 1B, and 1C, in an example embodiment of the invention, three different types of transducers that include angle beam transducers, comb transducers, and electromagnetic acoustic transducers (EMATs), can be used to generate selected guided wave modes in a structure, in this example, a pipe. An ultrasonic longitudinal transducer 10 mounted on an angle beam wedge 20 is called an angle beam transducer, which excites guided waves with a constant phase velocity with a particular incident angle. Individual elements 30 may be placed along an element spacing d along the axis of pipe 90 to be investigated.

Referring to FIG. 2A, excitation lines 210, 220 of two angle beam transducers placed on a pipe with different incident angles excite the longitudinal axisymmetric and flexural modes within the excitation zones 230, 240. Excitation zones exist at the cross of the excitation lines and phase velocity dispersion curves 250. If being excited simultaneously, a longitudinal comb transducer generates guided waves with a constant wavelength $\lambda$ equal to the spacing of the elements 30.

Referring to FIG. 3A, excitation lines 310, 320 of two comb transducers with different element spacing excite the longitudinal axisymmetric and flexural modes within the excitation zones 330, 340. Furthermore, every element may be driven individually with time delays to excite guided waves with various wave lengths. Time delays of the excitation signals may also be used to control the guided wave propagation directions. EMAT utilizes magnets 80 to generate a static magnetic field to drive coil wires with Lorentz forces whereby exciting guided waves with a constant wavelength $\lambda$. Here $\lambda/2$ equal to the width c of a magnet 80, illustrated in FIG. 1C.

Referring to FIG. 4A, excitation lines 410, 420 of two comb transducers or EMATs excite the torsional axisymmetric and flexural modes within the excitation zones 430, 440.

Figure 2:
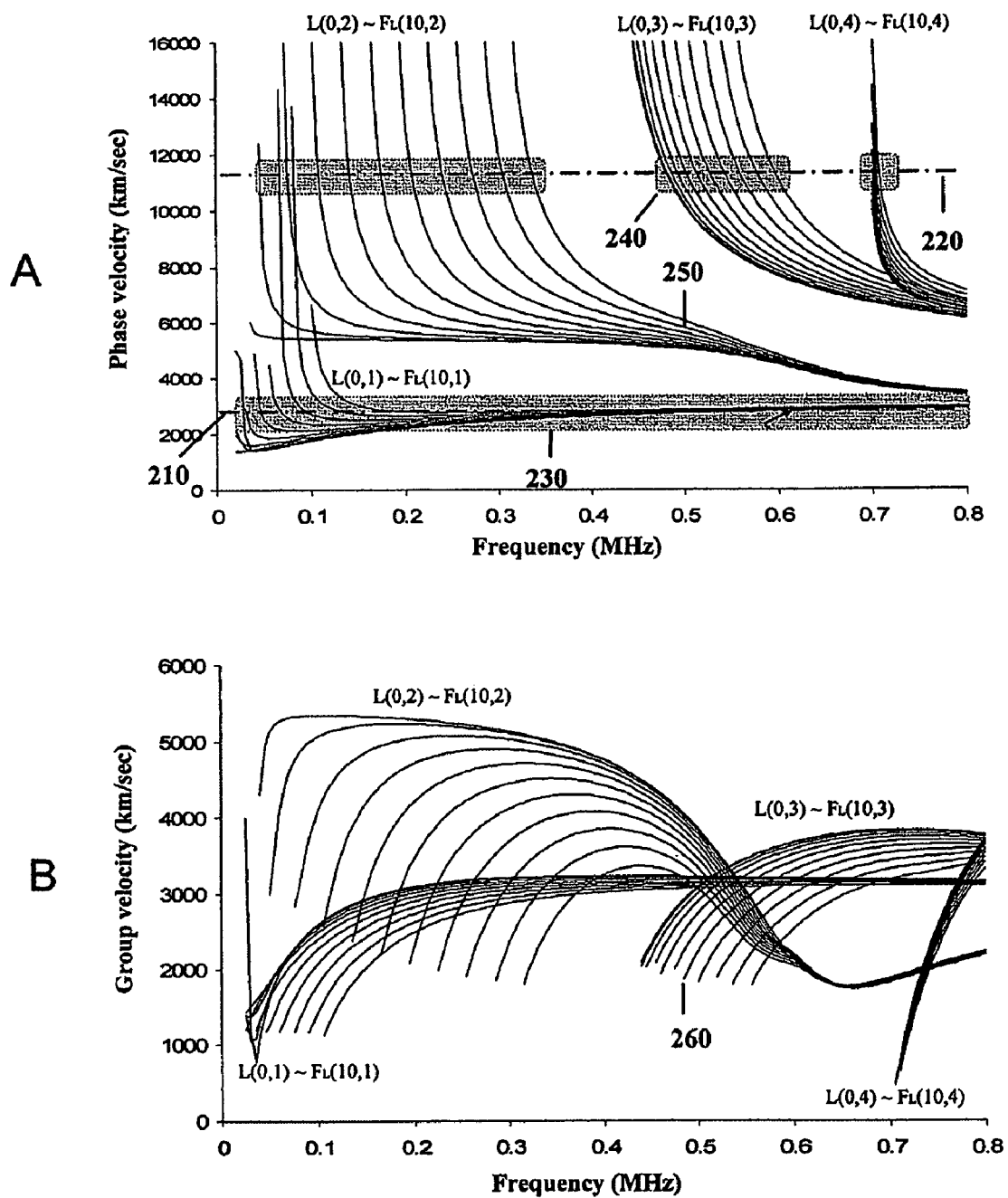
FIGS. 2A and 2B are examples of phase velocity dispersion curves and group velocity dispersion curves, respectively, for longitudinal guided waves in pipe. Sample potential excitation zones of angle beam transducers are also shown.
Figure 3:
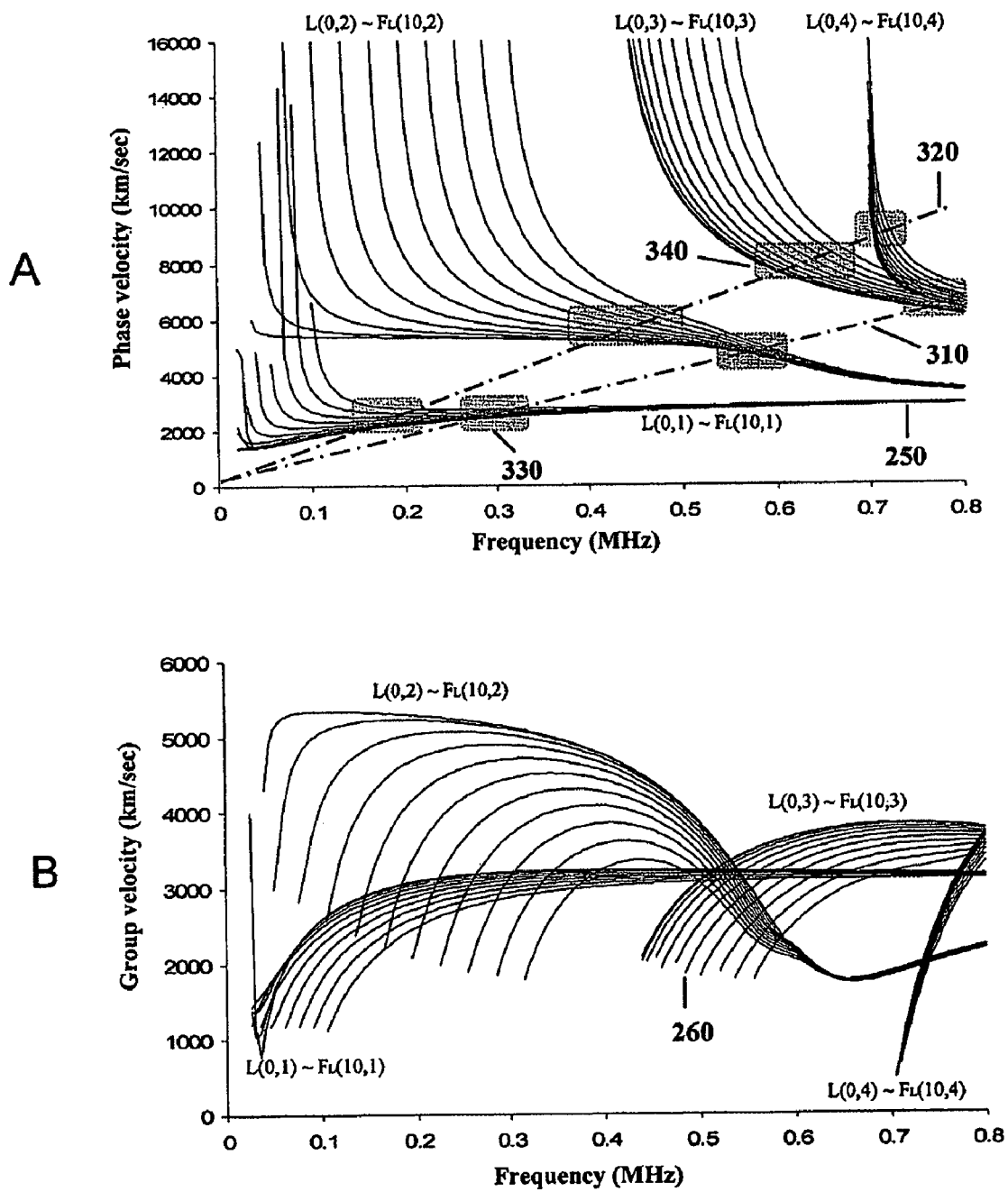
FIGS. 3A and 3B are examples of phase velocity dispersion curves and group velocity dispersion curves, respectively, for longitudinal guided waves in pipe. Sample potential excitation zones of comb transducers are also shown.
Figure 4:
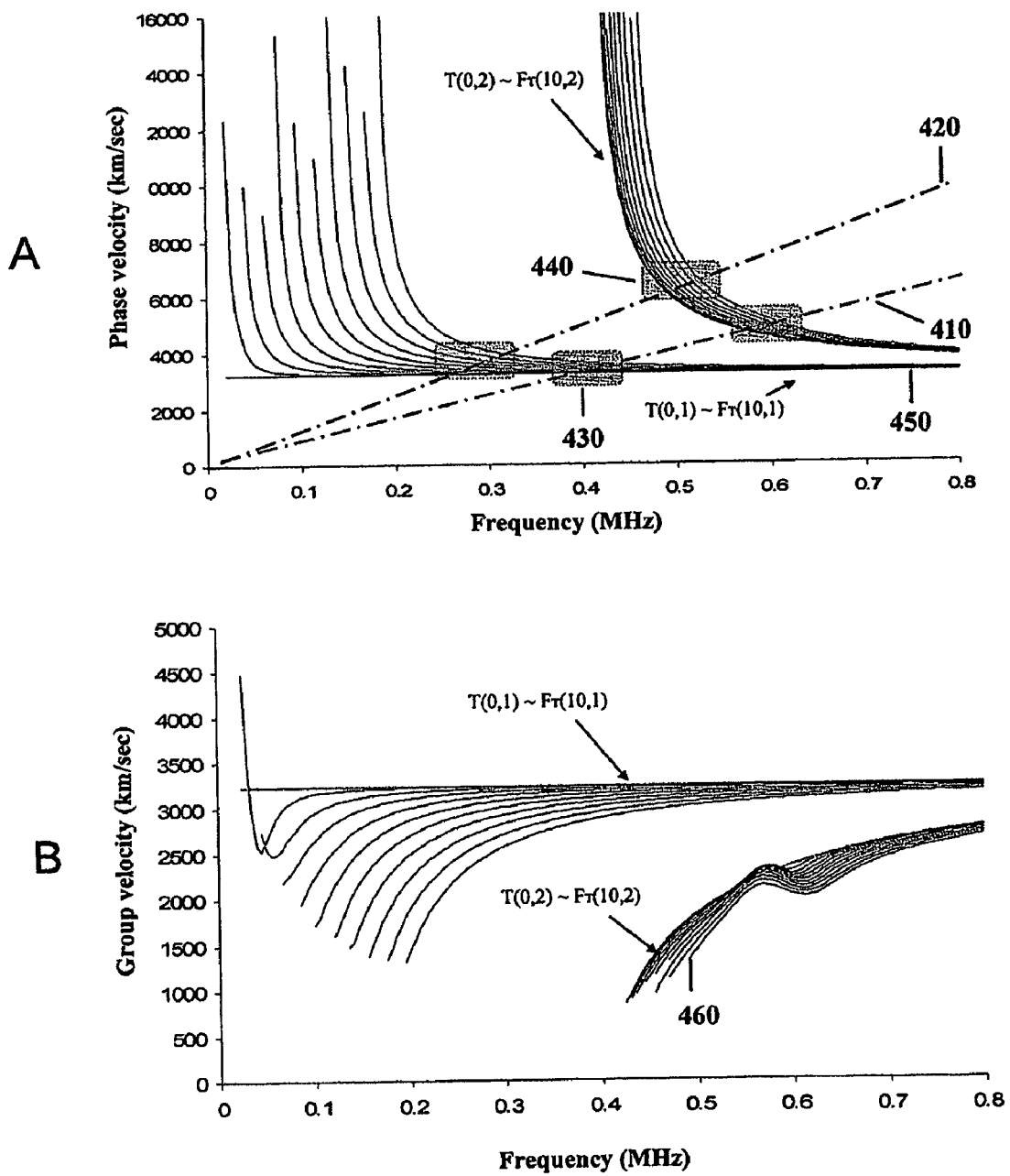
FIGS. 4A and 4B are examples of phase velocity dispersion curves and group velocity dispersion curves, respectively, for torsional guided waves in pipe. Sample potential excitation zones of EMATs or comb transducers are also shown.

Referring to FIGS. 2, 3, and 4, the sample group velocity dispersion curves 260 in a 4" schedule 40 steel pipe are derived from the phase velocity dispersion curves 250. The group velocity dispersion curves 260 indicate the guided wave velocities in pipe at different frequencies. When tuning frequency, if the group velocity of the generated wave group or groups significantly changes at various frequencies, a velocity compensation algorithm is used to obtain proper axial positioning of the reflector. In order to correctly locate reflectors, it is important that only one mode group with all the modes having close group and phase velocities should be excited at a single frequency.

Figure 5:
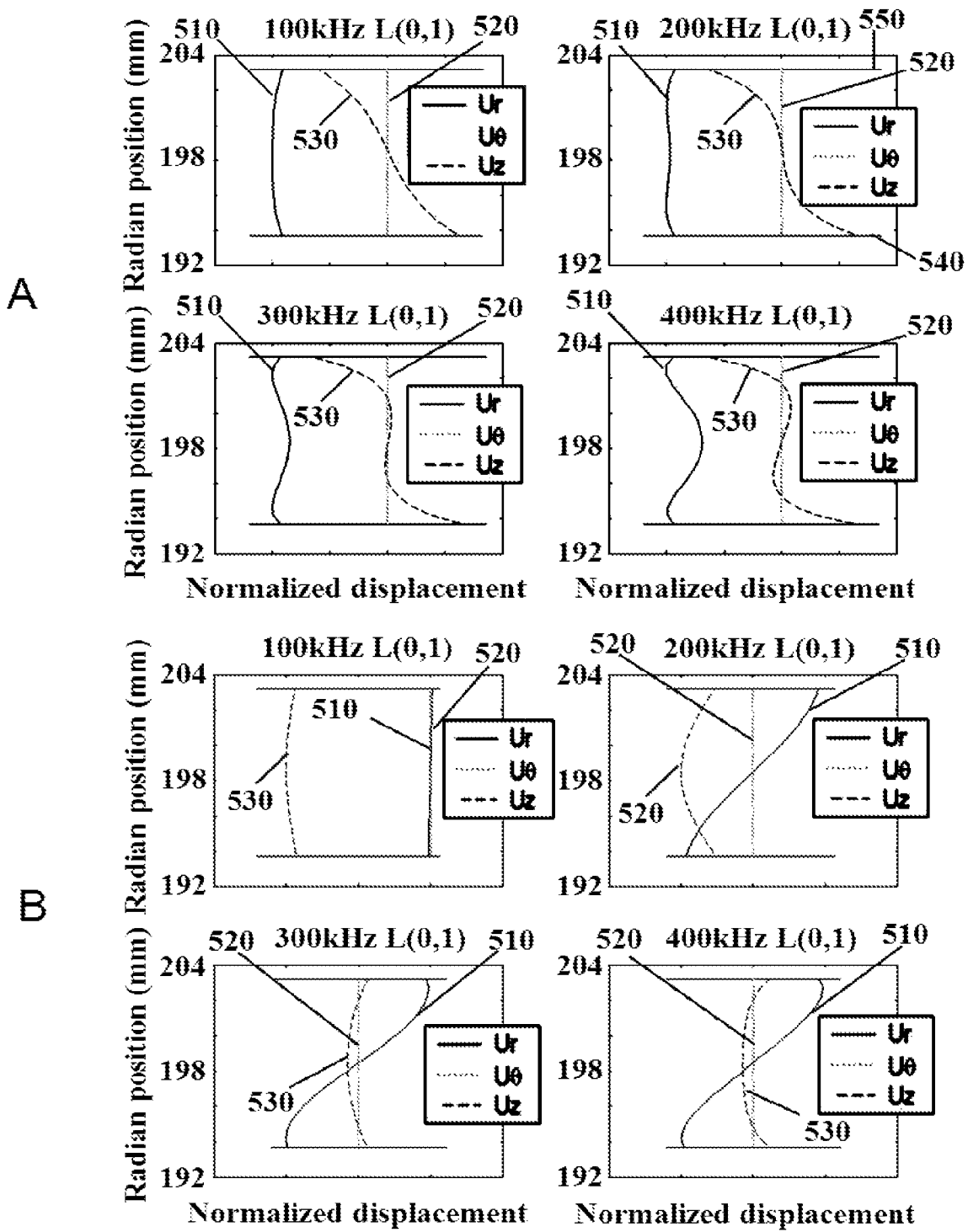
FIGS. 5A and 5B are examples of wave structures for different longitudinal axisymmetric modes and frequencies in pipe.

FIGS. 5A and 5B show sample wave structures of various wave modes and frequencies in a 16" schedule 30 steel pipe. In these figures, the lines 510 correspond to particle displacements in the radial direction between inner pipe surface 540 and outer pipe surface 550; the lines 520 corresponds to particle displacements in the circumferential direction; and the lines 530 corresponds to particle displacements in the axial direction.

Referring to FIG. 5B, the L(0,2) mode has significant different detection sensitivity, leaky potential, and attenuation values at different frequencies. The frequency tuning, therefore, will improve the inspection potential. In addition, the L(0,2) mode has dominant in-plane displacements at 100 kHz and the guided wave energy will rarely leak into fluid, although it has dominant in-plane displacements at 300 kHz and 400 kHz and will seriously leak into fluid. Therefore, the 100 kHz L(0,2) mode is good for fluid-loaded pipeline inspections, although the 300 kHz L(0,2) mode will not work.

Figure 6:
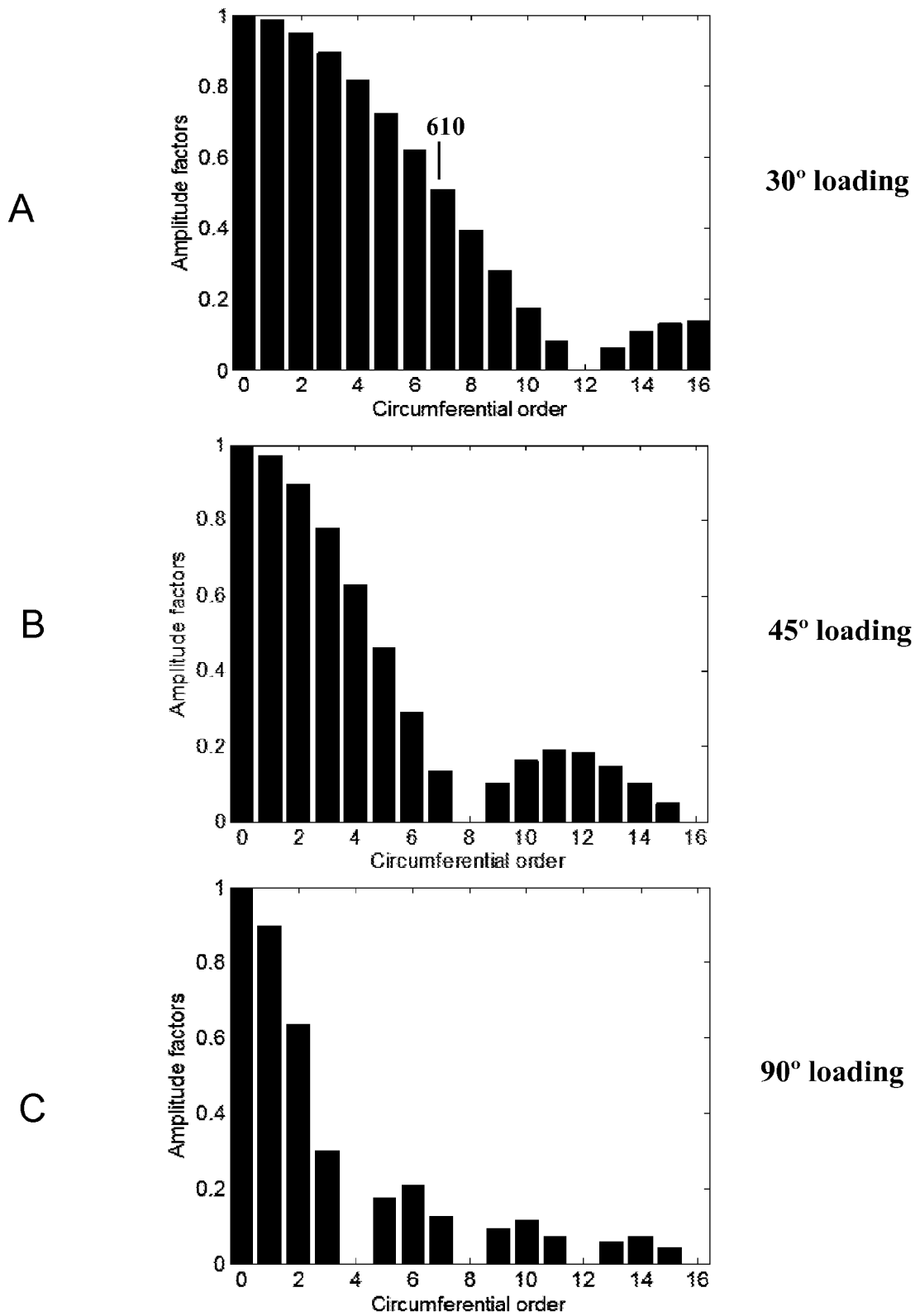
FIGS. 6A-6C are examples of normalized amplitudes of wave mode in one group varying with circumferential loading length.
Figure 7:
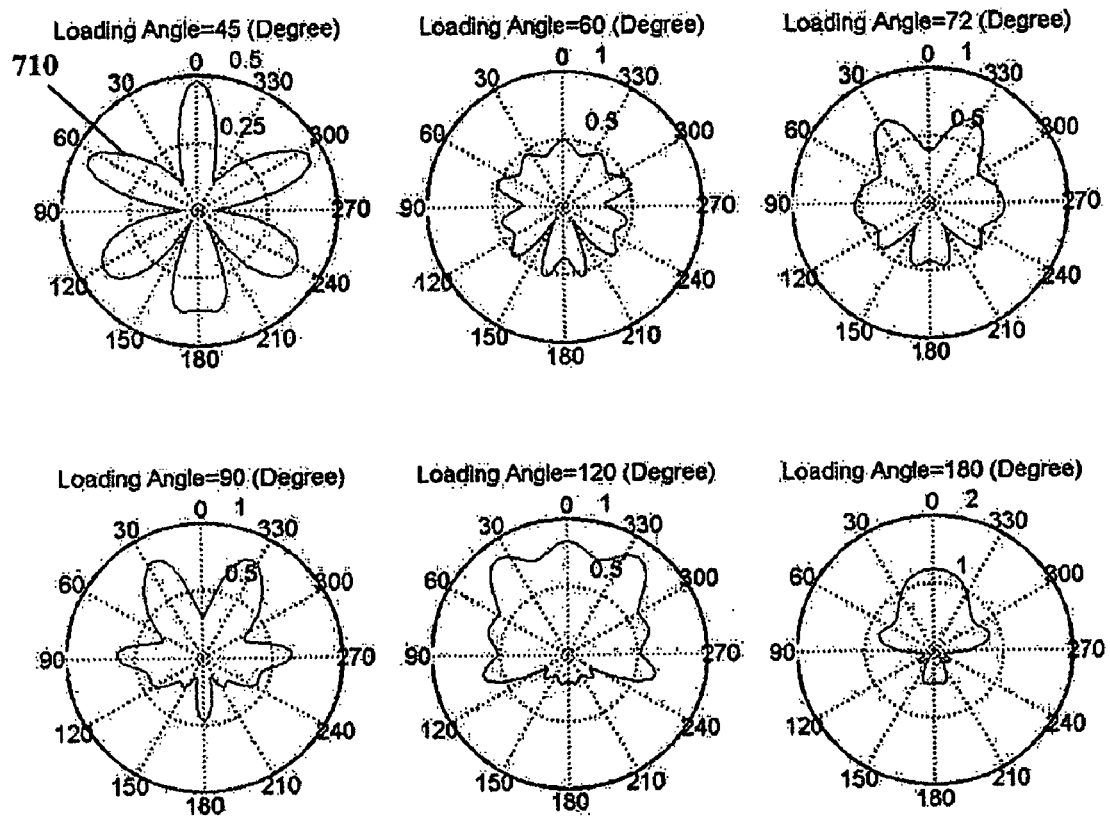
FIG. 7 shows several examples of angular profiles of a guided wave mode group in pipe when using various circumferential lengths.

Referring to FIGS. 6A-6C, sample amplitudes 610 of 50 kHz $T(0,1) \sim F_T(16, 1)$ mode in a 16" schedule 30 steel pipe have significant change when employing 30, 45, and 90 degree loadings. Angular profiles 710, as shown in FIG. 7, for one guided wave group propagating in pipe can be obtained by using the amplitudes 610 as weight functions to sum up the angular profiles of all the modes in this group. FIG. 7 shows sample angular profiles of 40 kHz $L(0,1) \sim F_L(m, 1)$ mode group (m=1, 2, 3, . . . ) excited by 45~180 degree loadings at 240" away from the loadings in a 16" schedule 30 steel pipe. Referring to FIG. 7, different circumferential loading lengths will cause a guided wave group to naturally focus at various spots. Use of more loading lengths, therefore, will often lead to a more complete focal scan.

Figure 8:
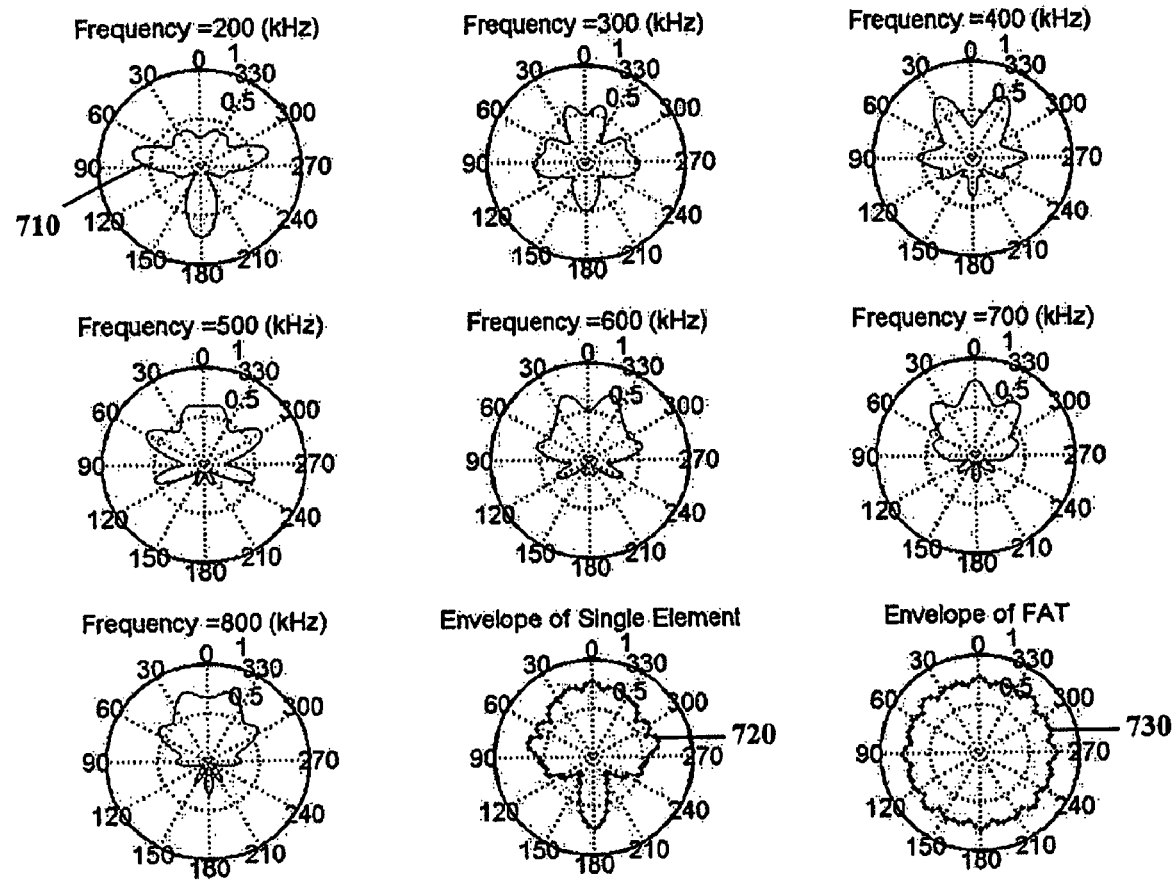
FIG. 8 shows examples of angular profiles and their envelopes over a particular frequency range.

FIG. 8 shows sample angular profiles 710 of $L(0,1) \sim F_L(m, 1)$ mode group (m=1, 2, 3, . . . ) and their envelops 720 and 730 at 106" away from the 45° loading in a 4" schedule 40 steel pipe over a frequency range: 200 kHz~800 kHz. The center of the loading is at 0°. An angular profile 710 at a single frequency may have some natural focal spots and blind spots at a particular distance. The envelop 720 of the angular profiles 710 over the whole frequency range has more focal points and less blind zones, and then covers more regions. If there are 7 more loadings located at every 45°, the envelop 730 of all the angular profiles over the frequency range by employing every loading has no blind zone and totally covers the cross-sectional region.

Figure 9:
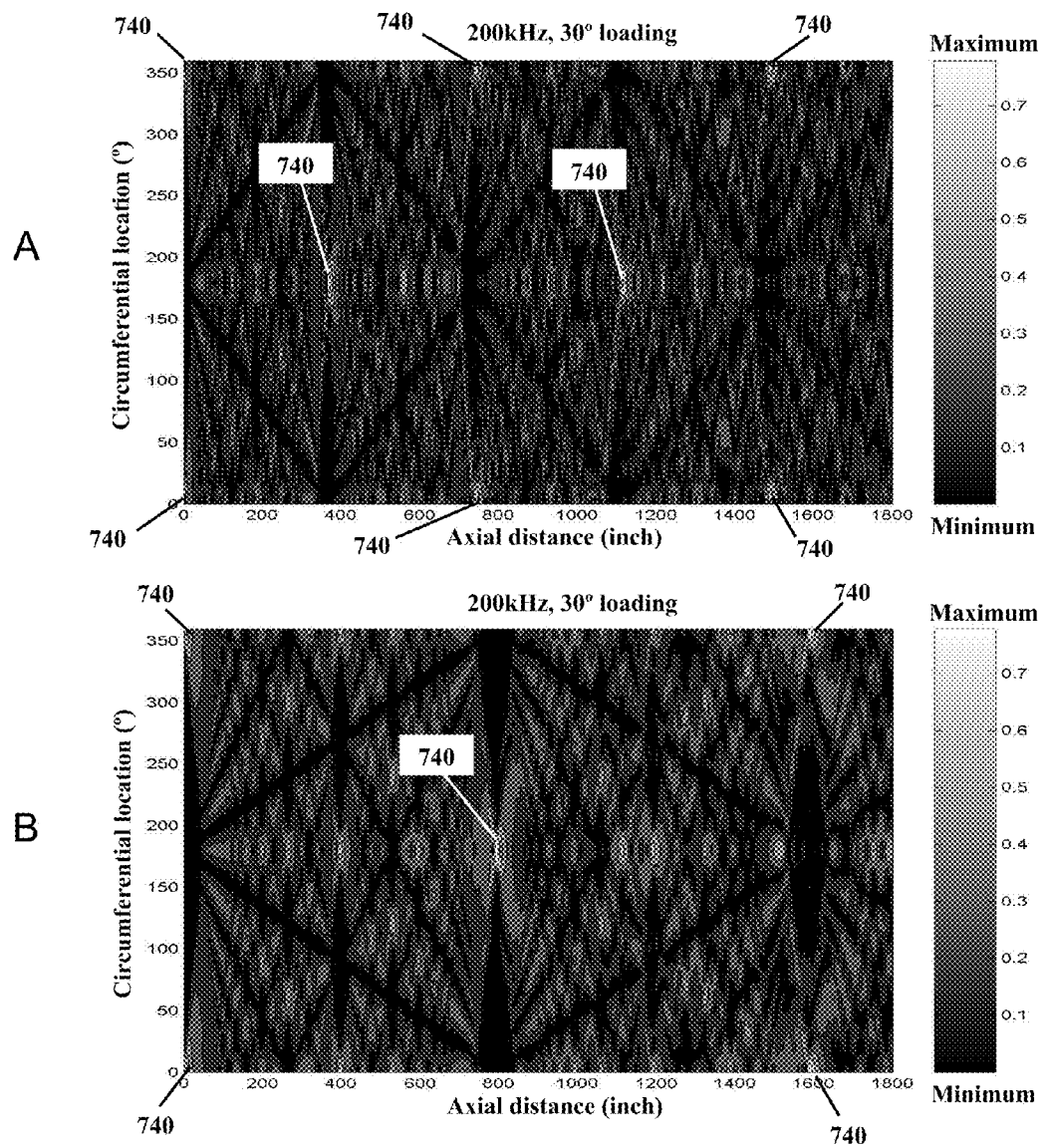
FIGS. 9A, 9B, 10A, 10B, 11A, and 11B show theoretical positioning of natural focal points in a pipe due to sensor location, frequency, and loading length variables.
Figure 10:
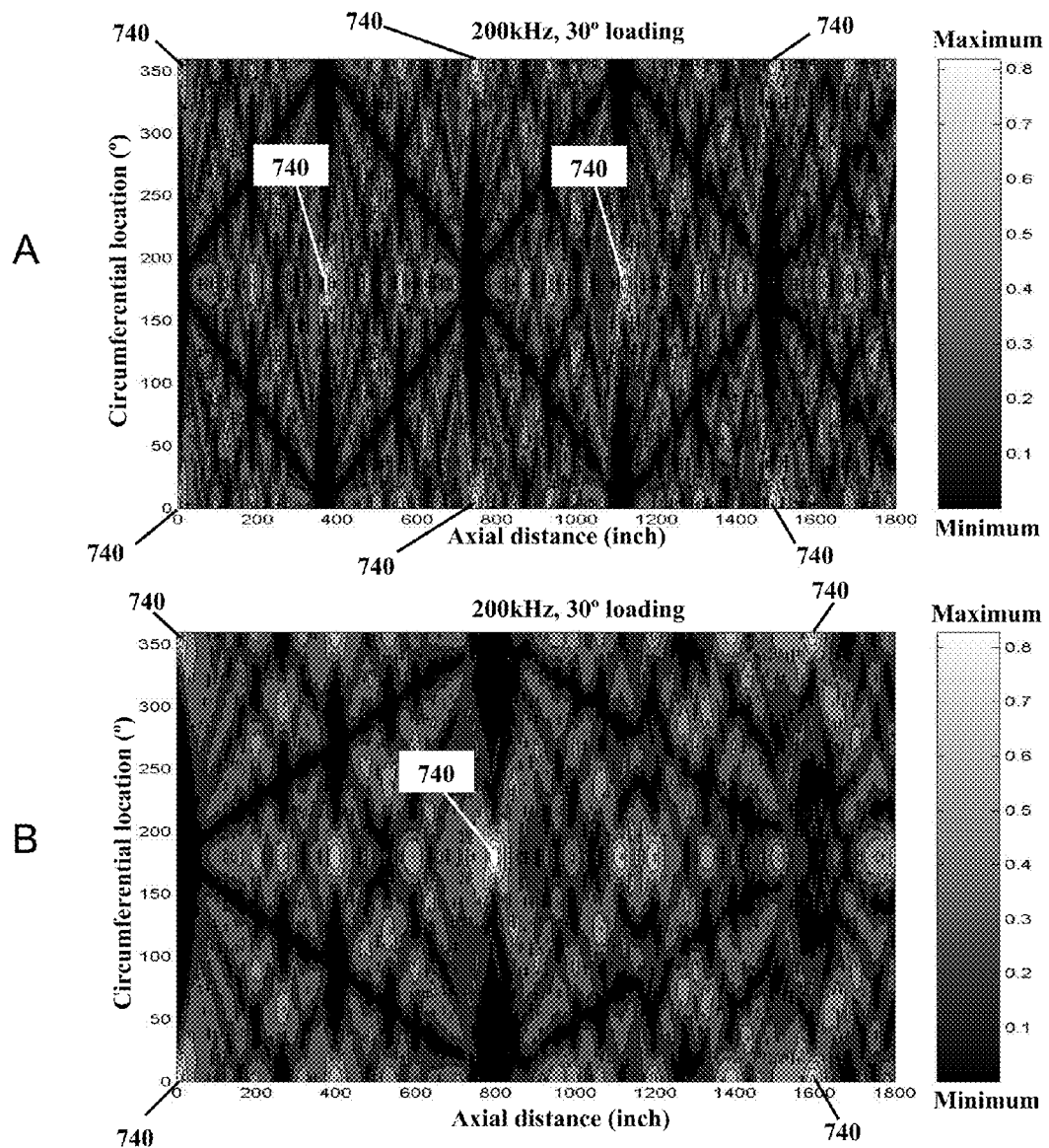
Figure 11:
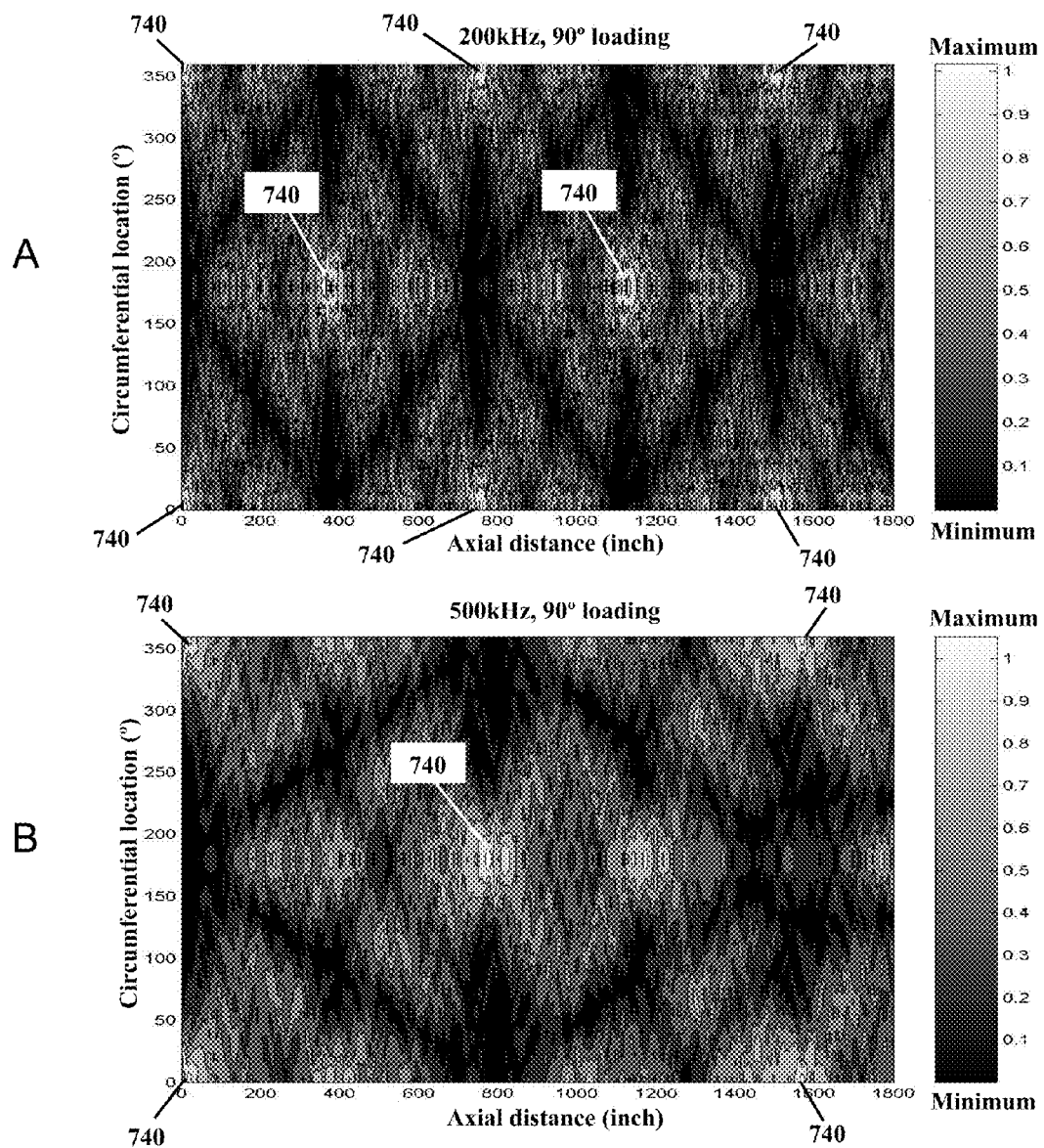

Referring to FIGS. 9A, 9B, 10A, 10B, 11A, and 11B, some theoretical results are illustrated to show how the natural focal spot 740 moves around the pipeline structure from 0 to 360 degrees and over an axial distance of 360 in. (30 feet). FIG. 9A shows a result for the 200 kHz L(0,1)~FL(m,1) mode group and FIG. 9B shows a result for the 500 kHz L(0,1)~FL(m,1) mode group with a 30 degree circumferential loading. Notice the high intensity spots 740; representing the natural focal points. Superimposing all of these results leads to practically almost complete coverage of the pipe being inspected. Various degrees of partial loading around the circumference of the pipe are considered. Loads that are 30, 45, and 90 degrees are shown in FIGS. 9, 10 and 11 at two different frequencies. The vertical focal point is larger, and again changes position with frequency as well, A at 200 KHz and B at 500 KHz. Again, referring to FIGS. 9, 10, and 11, a superposition of many frequencies and many loading lengths even improves the complete inspection potential of the pipe further.

Figure 12:
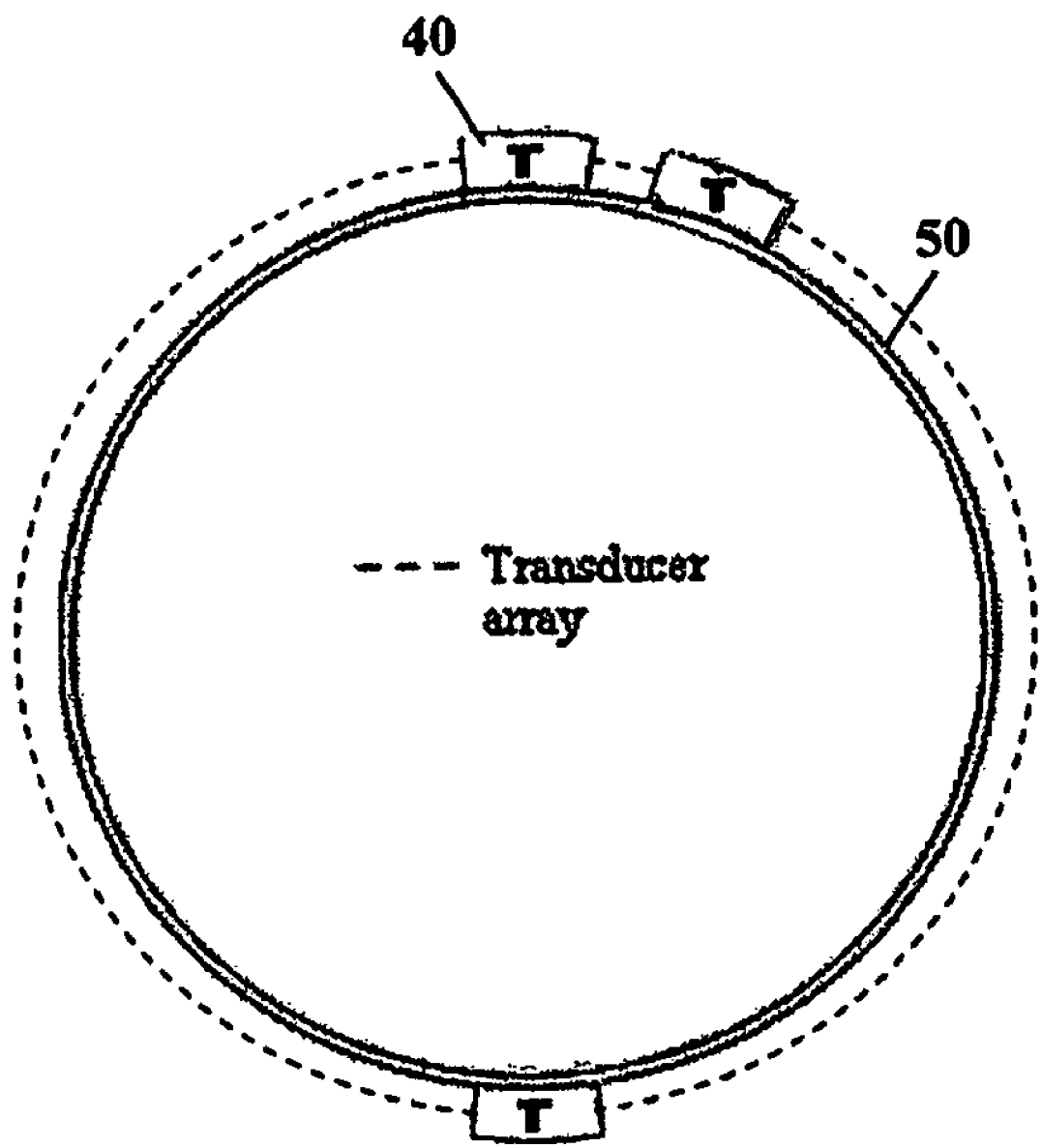
FIG. 12 illustrates an example of abundant transducers mounted on the outer surface of a pipe.
Figure 13:
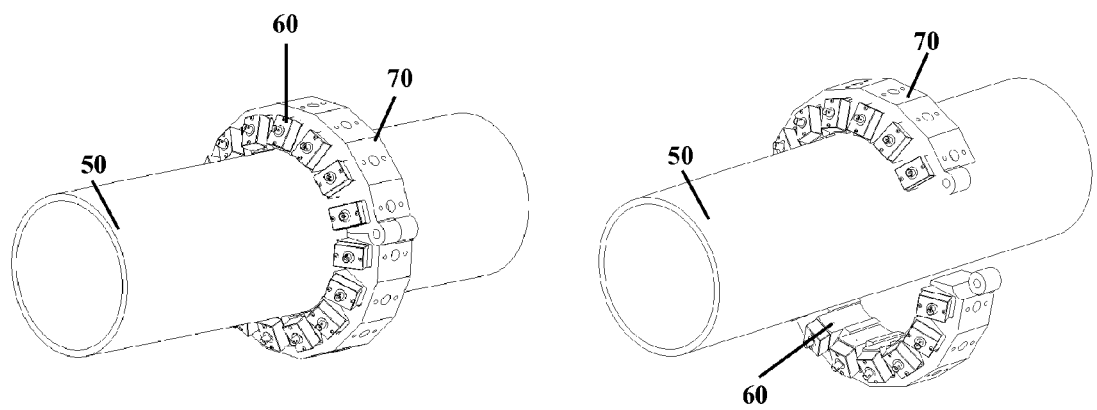
FIG. 13 shows sample designs of an angle beam transducer array wrapped around a pipe for pipe inspection.

FIG. 12 shows schematics of a transducer ring mounted on pipe 50. Each transducer 40 can be driven individual or in a group of N (N is a positive integer and no more than the maximum transducer numbers in the ring). FIG. 13 shows a designed ring of angle beam transducers 60 on pipe 50. A frame 70 is used to hold the transducers 60.

Figure 14:
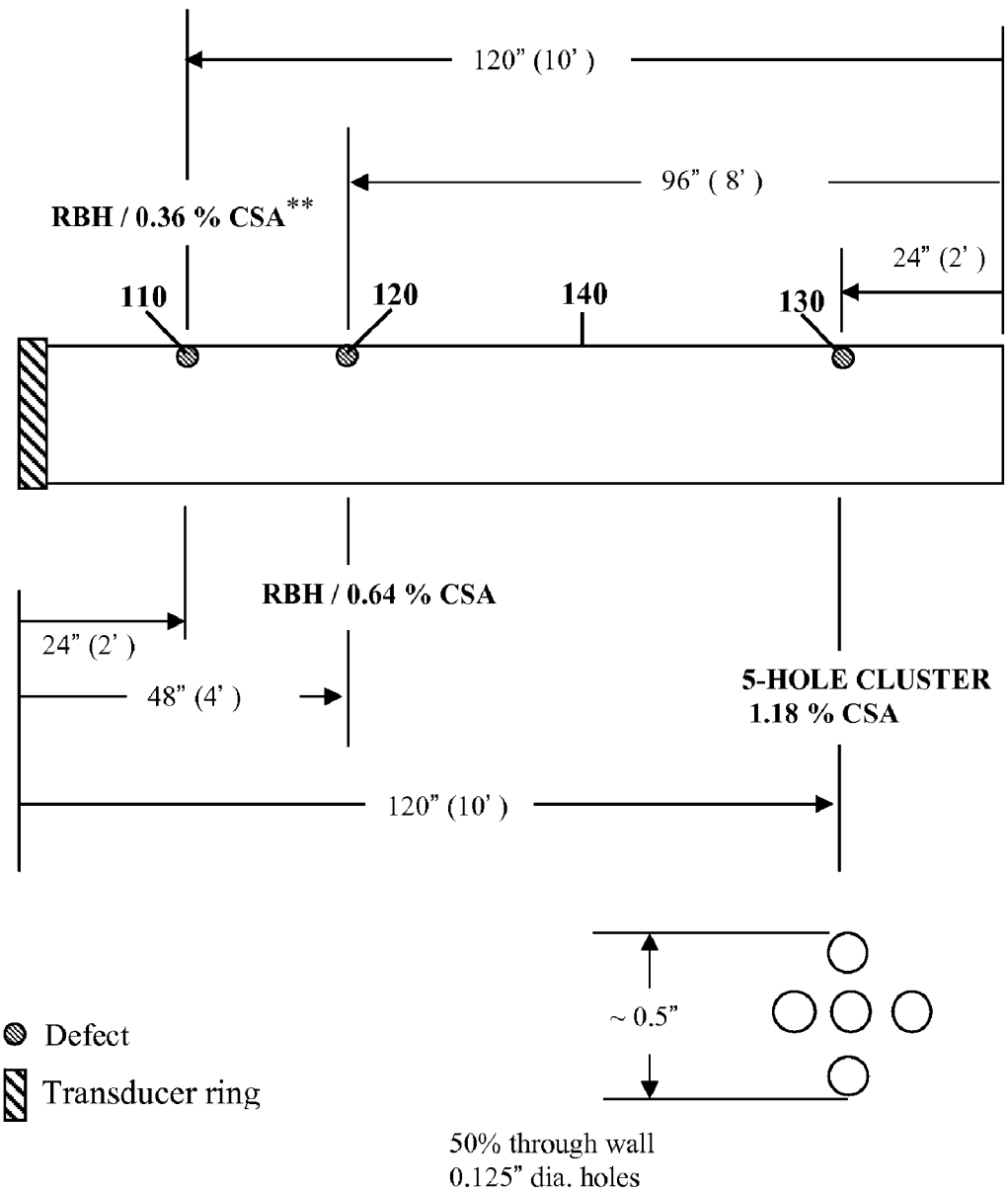
FIG. 14 illustrates the schematics of an experimental test specimen.

FIG. 14 illustrates the schematics of a 4" schedule 40 steel pipe 140 with three defects 110, 120, and 130. The 0.36% CSA round-bottom hole 110 is located in the inner wall of the pipe; the 0.64% CSA round-bottom hole 120 and 1.18% CSA 5-hole cluster 130 are located in the outer wall of the pipe 140.

Figure 15:
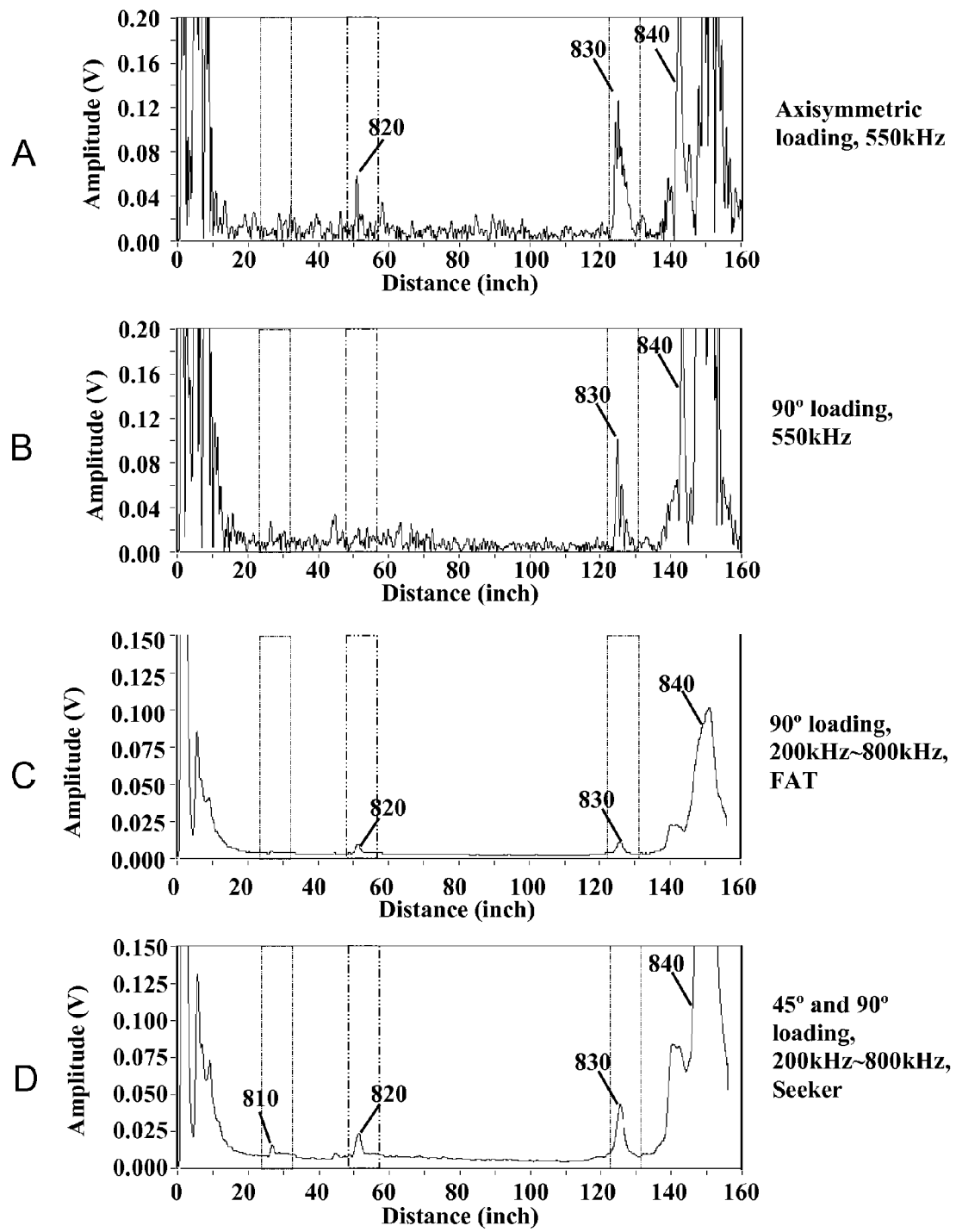
FIG. 15 provides illustrative examples of experimental results of pipe inspections by employing the different techniques.

Referring to FIG. 15, sample experimental results show benefits of the technique provided. FIG. 15A shows the inspection results for the pipe 140 (shown in FIG. 14) by using an angle beam transducer ring to generate the 550 kHz axisymmetric L(0,1) mode. A large reflection 830 from the 1.18% defect 130 and a small reflection 820 from the 0.64% defect 120 were clear, although no reflection from the 0.36% defect 110 has been observed. If a user uses one single 90° angle beam transducer to generate the $L(0,1) \sim F_L(m, 1)$ modes to do the inspection at 550 kHz, only the reflection 830 from the defect 130 was found, as shown in FIG. 15B. FIG. 15C shows the inspection results by employing the FAT technique by exciting four 90° angle beam transducers individually over the frequency range 200 kHz~800 kHz. Referring to FIG. 15C, the FAT technique significantly improves the signal-to-noise ratio and has two defect reflections 820 and 830, although the 0.36% defect 110 still was not found. FIG. 15C is the final display of signal processing of hundreds of inspection waveforms. FIG. 15D shows the inspection results by using the new invented system with four 90° angle beam transducers and eight 45° angle beam transducers over the frequency range 200 kHz~800 kHz. Referring to FIG. 15D, all three defect echoes have been found by utilizing this technique. FIG. 15C is the final display of signal processing of more than 1000 inspection waveforms, which involves different circumferential loading lengths, transducer locations, frequencies, and wave modes. All the above inspections have a backwall reflection 840 from the pipe end. All defects were found.

What is claimed is:

1. A method for examining a pipe, comprising:
 arranging and pulsing sensors around a circumference of a pipe that when varying a number and position of sensors that are excited at least singularly, creates at least one of axisymmetric and non-axisymmetric wave forms and natural focal points in at least one of pipe, in pipe elbows, and beyond pipe elbows and when multiplexed around a circumference of the pipe, moves a focal spot to different positions in the pipe to find defects in the pipe wherein interpretation of results of received wave forms is made in a more timely manner by combining resulting waveforms into a single waveform or reduced number of waveforms.

2. The method according to claim 1, further comprising:
frequency tuning to move the natural focal points to different positions throughout the pipe, wherein wave structures excited by the sensors are changed to enhance detection sensitivity for various defects in the pipe.

3. The method according to claim 1, further comprising:
changing a circumferential loading length and position by varying at least one of the number and position of sensors that are excited at least singularly around the circumference of the pipe to move the natural focal points to different regions in the pipe to find defects in the pipe.

4. The method according to claim 1, further comprising:
signal processing wherein multiple signals with different focal spot positions are processed and combined to produce a reduced number of final waveforms that show defect axial positions in the pipe.

5. The method according to claim 1, wherein multiplexing a sending and receiving of the sensors around the circumference of the pipe produces and receives multiple non-axisymmetric waveforms with different focal spot positions that when received are processed and combined to lead to a reduced number of waveform displays.

6. The method according to claim 1, wherein the sensors are pulsed using non-axisymmetric modes with natural focal spots with just partial loading of the pipe in a circumferential direction, thereby providing an ability to inspect at least one of hidden and inaccessible pipeline structures.

7. The method according to claim 1, wherein the method detects defects that are approximately 0.1% cross sectional area and above over a frequency range 200 kHz to 800 kHz.

8. The method according to claim 1, wherein the method detects defects that are approximately 3% cross sectional area and above over a frequency range 20 kHZ to 150 kHZ.

9. The method according to claim 1, wherein the method detects defects that are approximately 0.01% cross sectional area and above in a thin walled tube using frequencies higher than 800 kHz.

10. The method according to claim 1, wherein the pipe has a pipe elbow.

11. The method according to claim 1, wherein an excitation region is swept through phase velocity dispersion curve space in a horizontal direction for selected phase velocity values using angle beam wedges and frequency sweeping.

12. The method according to claim 1, wherein an excitation region is swept along an angled line of slope d from an origin through phase velocity dispersion curve space by using one of comb and EMAT sensors with a specific sensor element spacing that correlates to a slope d.

13. The method according to claim 1, wherein there is partial loading only around a circumference of the pipe and given sufficient bandwidth, inspection of a complete circumference of the pipe is still provided along a length of the pipe.

14. The method according to claim 1, wherein shear type sensors are used.

15. The method according to claim 1, wherein longitudinal type sensors are used.

16. The method according to claim 1, wherein a phased array comb type transducer is placed on one of an angle beam wedge and directly onto a pipe surface in an abundant sensor arrangement around a circumference of the pipe to produce horizontal activation lines in dispersion curve space, each line determined by a unique set of time delays in each comb sensor and the wedge angle when a wedge is used.

17. The method according to claim 16, wherein additional time delays are applied to each comb sensor around the circumference of the pipe added to the set of time delays used to generate the specific horizontal activation line, to produce phased array focal spots in the pipeline in addition to new natural focusing spots.

18. The method according to claim 1, further comprising:
searching a phase velocity dispersion curve space and isolating positions where defects are found, wherein when a dispersive mode is used, defect location analysis is performed.

19. The method according to claim 1, wherein the pipe is fluid loaded, wherein dominant inplane displacement on an inner surface is purposely excited to allow for inspection to occur, defect detection sensitivity is decreased such that only larger defects are found because of energy leakage to the fluid inside the pipe.

20. The method according to claim 1, wherein EMAT shear sensors are used to reduce energy leakage to a fluid inside the pipe, therefore maintaining sensitivity to find defects.

21. A method according to claim 1, further comprising:
utilizing partial loading around a circumference of the pipe that with one signal finds a defect at some particular axial and circumferential position around the pipe at a distance.

22. A method according to claim 1, further comprising:
utilizing predicted focusing profiles for partial loading to determine a circumferential position of a defect.

23. The method according to claim 1, further comprising:
changing a receiving element region by varying at least one of the number of sensors that are received and their position around the circumference of the pipe to receive all possible modes that are reflected.

* * * * *